United States Patent [19]

Endo et al.

[11] 4,049,495
[45] Sept. 20, 1977

[54] PHYSIOLOGICALLY ACTIVE SUBSTANCES AND FERMENTATIVE PROCESS FOR PRODUCING THE SAME

[75] Inventors: Akira Endo; Masao Kuroda; Akira Terahara; Yoshio Tsujita; Chihiro Tamura, all of Tokyo, Japan

[73] Assignee: Sankyo Company Limited, Tokyo, Japan

[21] Appl. No.: 637,673

[22] Filed: Dec. 4, 1975

Related U.S. Application Data

[62] Division of Ser. No. 576,651, May 12, 1975, Pat. No. 3,983,140.

[30] Foreign Application Priority Data

June 7, 1974    Japan .................................. 49-64823

[51] Int. Cl.² ............................................ C12D 13/02
[52] U.S. Cl. ..................................... 195/36 R; 195/81
[58] Field of Search ................................ 195/81, 36 R

[56] References Cited
U.S. PATENT DOCUMENTS

| | | | |
|---|---|---|---|
| 3,297,526 | 1/1967 | Gaeumann et al. | 195/36 R |
| 3,909,362 | 9/1975 | Jiu et al. | 195/81 |

Primary Examiner—Alvin E. Tanenholtz

Attorney, Agent, or Firm—Flynn & Frishauf

[57] ABSTRACT

Physiologically active substances ML-236 of the formula

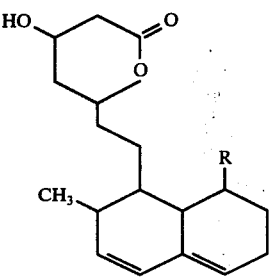

(I)

wherein R is hydrogen atom, hydroxy group or 2-methyl-butyryloxy group having cholesterol- and lipid-lowering effects in blood and liver and thus utility as hypocholesteremic and hypolipemic medicaments. They are obtained by cultivation of an ML-236-producing microorganism belonging to the genus *Penicillium* in a culture medium and subsequent recovery thereof from a cultured broth.

5 Claims, 6 Drawing Figures

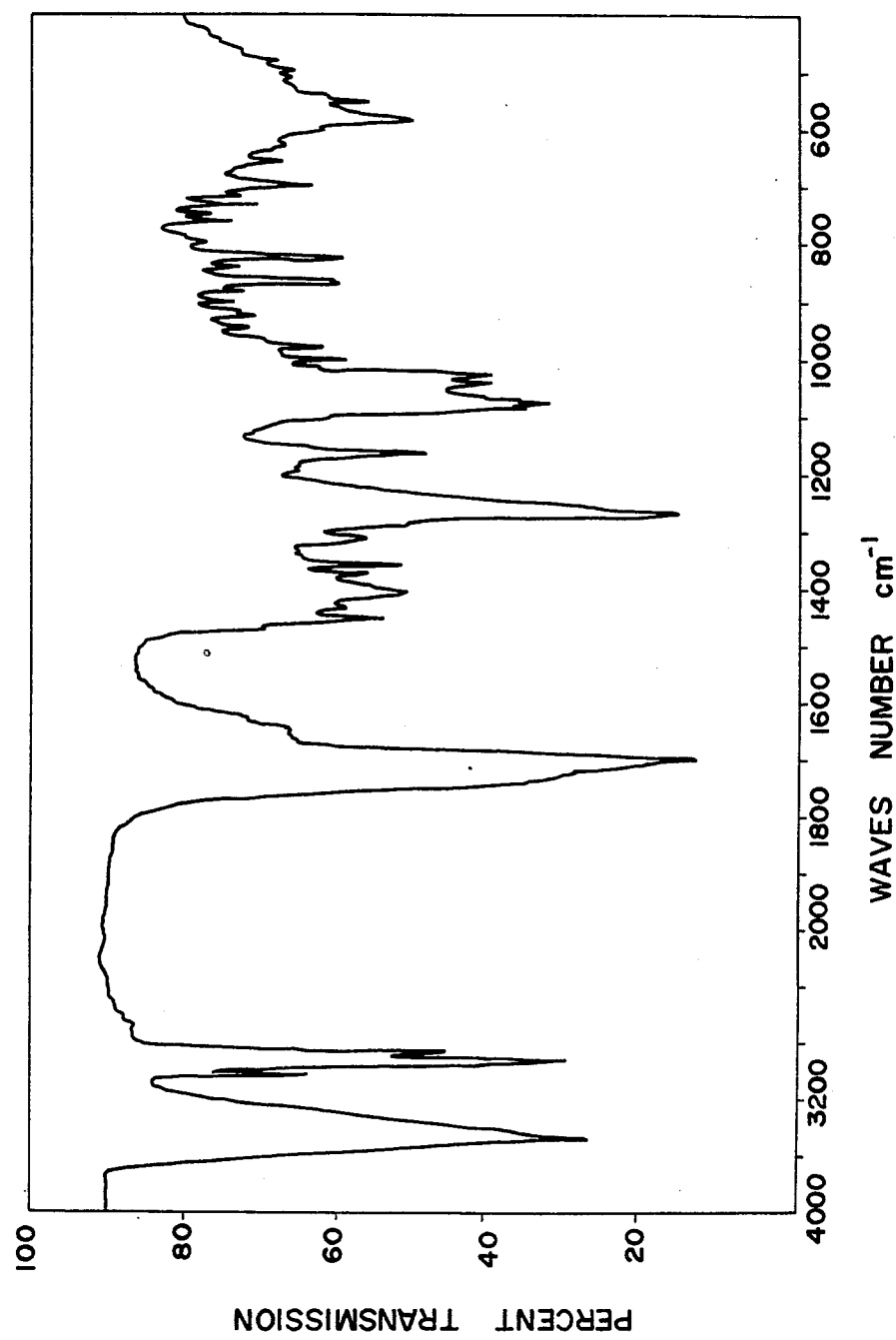

PHYSIOLOGICALLY ACTIVE SUBSTANCES AND FERMENTATIVE PROCESS FOR PRODUCING THE SAME

This is a (X) division, of application Ser. No. 576,651, filed May 12, 1975 now U.S. Pat. No. 3,983,140.

This invention relates to new physiologically active substances and a fermentative process for producing the same.

More particularly, it is concerned with a new class of physiologically active substances (hereinafter referred to as "ML-236") having the formula

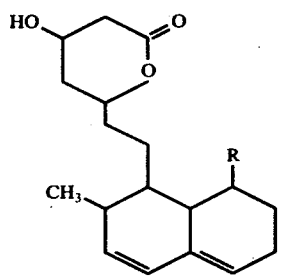

(I)

wherein R is hydrogen atom, hydroxy group or 2-methylbutyryloxy group (—OCOCH(CH$_3$)CH$_2$CH$_3$) and also with a process for the production of the substances ML-236 by cultivation of an ML-236-producing microorganism belonging to the genus *Penicillium*.

The new substances ML-236 of this invention have excellent physiological activities for medicinol use, more specifically, an inhibition activity of cholesterol biosynthesis, an antiantherosclerosis activity and an antihyperlipemia activity.

One cause of such diseases as atherosclerosis, hyperlipemia and so on is now considered to be owing to cholesterol deposit within a living body, especially in the intima of arteries.

Under these circumstances, we have made systematic studies on substances obtainable from cultured broth of microorganisms about their inhibition activities of cholesterol biosynthesis, from a standpoint wherein inhibition of cholesterol biosynthesis may be effective in preventing and treating such diseases and, as a result, it has been found that the substances ML-236 can be isolated from a cultured broth of a microorganism belonging to the genus *Penicillium* and also that the substances ML-236 possess potent cholesterol- and lipid-lowering effects in blood and liver.

It is, accordingly, a primary object of this invention to provide a new group of the substances ML-236 of the above formula (I) which are highly useful as hypochloesteremic agents and hypolipemic agents for the treatment of atherosclerosis, hyperlipemia and like diseases.

Another object of this invention is to provide a process for the fermentative production of the valuable substance ML-236 by cultivation of an ML-236-producing microorganism belonging to the genus *Penicillium*.

Other objects and advantages of this invention will be apparent from the description as shown hereunder.

In one aspect of this invention, there are provided the substances ML-236 of the formula (I) as briefly explained hereinabove. It has now been clarified that the substances ML-236 of the formula (I) are separated into 3 kinds of substances which are designated as "ML-236A", "ML-236B" and "ML-236C," respectively, and the respective plane structures thereof have been clarified as defined below, with the NMR, mass, IR, and UV spectra and X-ray diffractiometries thereof.

ML-236A (Ia)

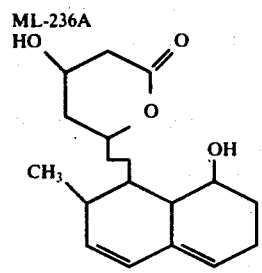

ML-236B (Ib)

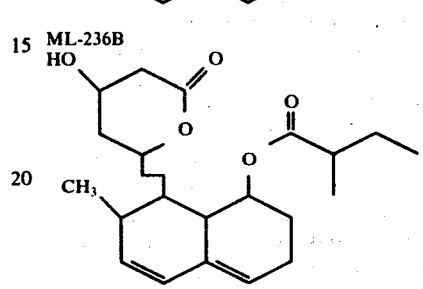

ML-236C (Ic)

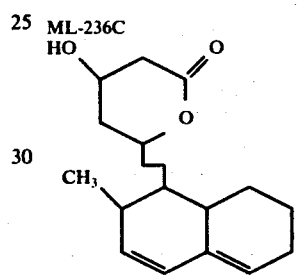

The physico-chemical properties of the substances ML-236A, ML-236B and ML-236C are summarized as shown below.

| | | ML-236 A | ML-236 B | ML-236 C |
|---|---|---|---|---|
| Nature | | oily (neutral) | white scales (neutral) | oily (neutral) |
| m.p. | | — | 149–151° C. | — |
| Elementary analysis (%) | C | 70.18 | 70.68 | 74.04 |
| | H | 8.75 | 8.56 | 8.58 |
| | O | 21.07 | 20.76 | 17.38 |
| Molecular Weight (Mass spectrum) | | 306 | 390 | 290 |
| Molecular Formula | | C$_{18}$H$_{26}$O$_4$ | C$_{23}$H$_{34}$O$_5$ | C$_{18}$H$_{26}$O$_3$ |
| UV spectrum (Methanol) | | As shown in FIG. 1 | As shown in FIG. 3 | As shown in FIG. 5 |
| IR spectrum (KBr) | | As shown in FIG. 2 | As shown in FIG. 4 | As shown in FIG. 6 |
| Solubility | | Soluble in methanol, ethanol, acetone, ethyl acetate, chloroform and benzene Insoluble in n-hexane and petroleum ether | | |
| R$_f$ value (TLC : Silica gel G) | n-hexane-acetone (1:1) | 0.21 | 0.46 | 0.52 |
| | dichloromethane-ethyl acetate (7:3) | 0.08 | 0.21 | 0.27 |

In FIGS. 1 through 6 hereof, FIG. 1 shows the ultraviolet absorption spectrum of ML-236A exhibiting maxima at 229, 236 and 245 mμ, respectively; and FIG. 2 shows the infrared absorption spectrum of ML-236A showing absorption bands at 3350, 3300 and 1725 cm$^{-1}$, respectively.

FIG. 6 shows the infrared absorption spectrum of ML-236C showing absorption bands at 3350 and 1700 cm$^{-1}$, respectively.

Figure 1:
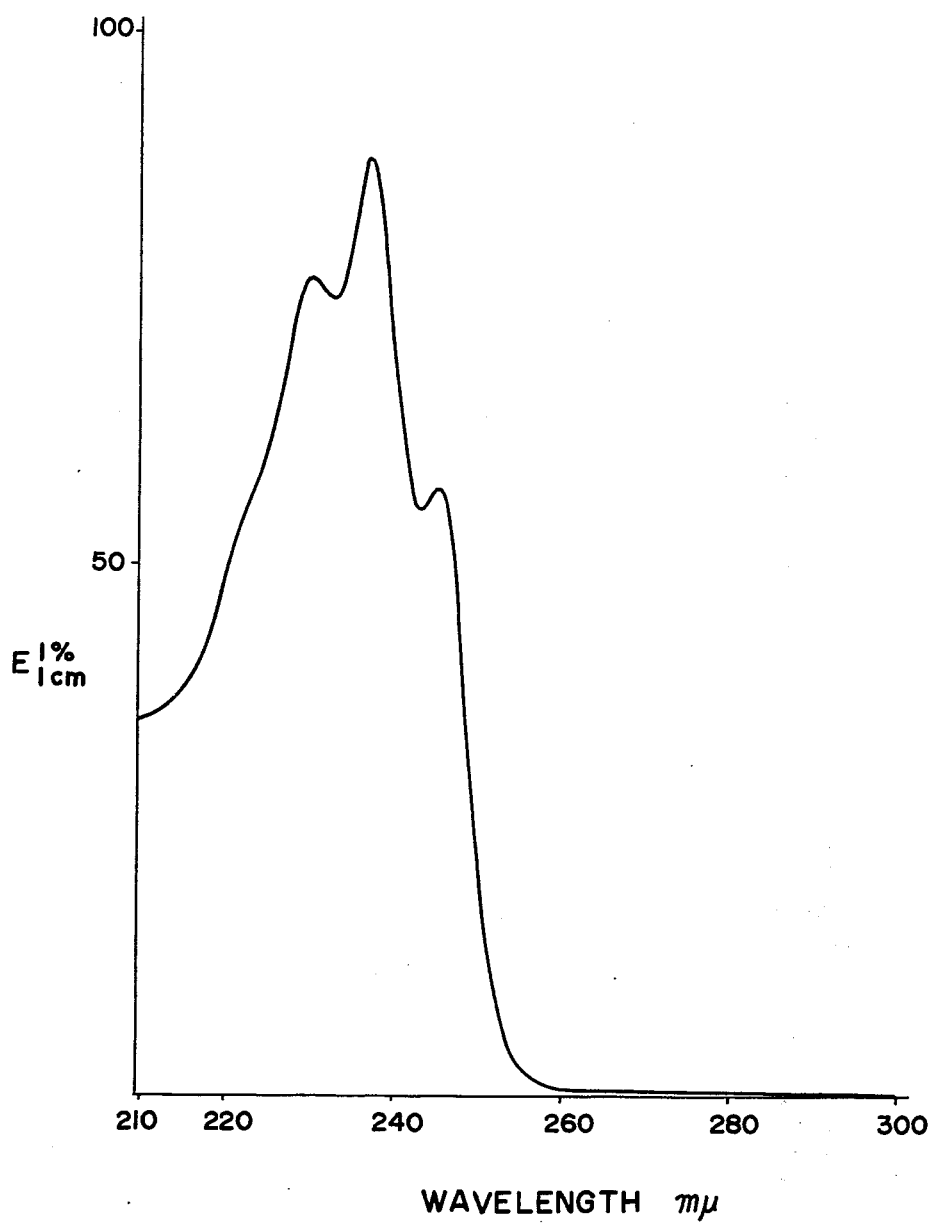
Figure 2:
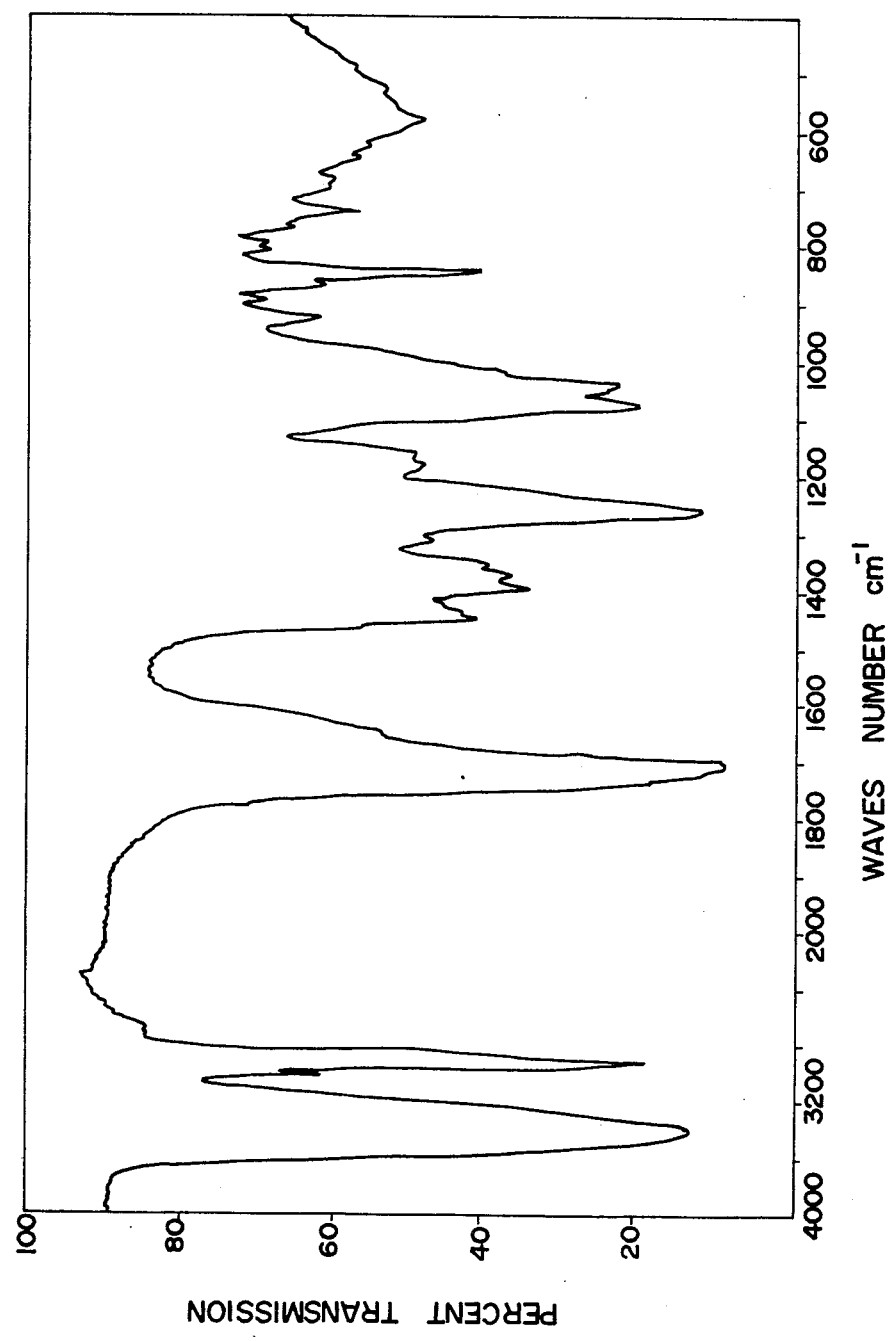
Figure 3:
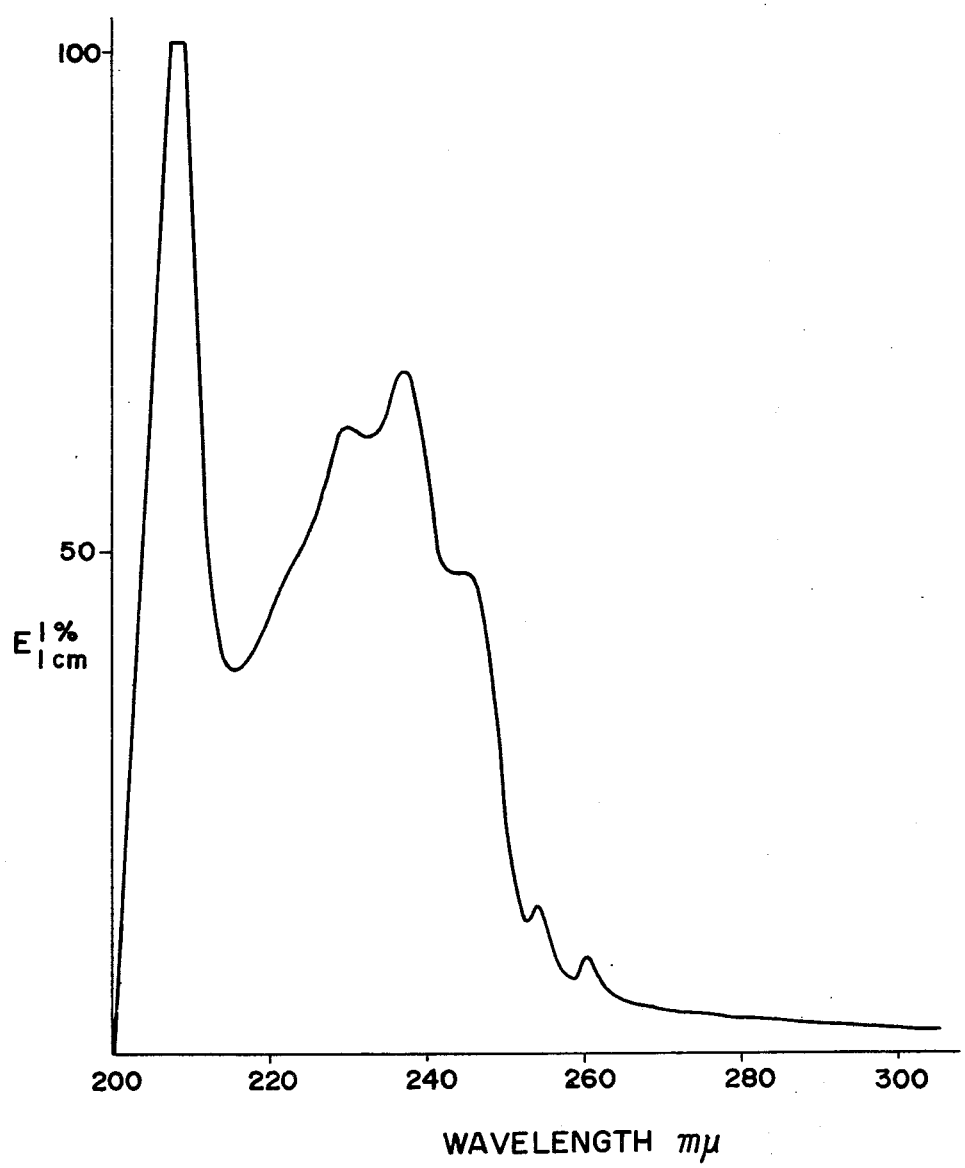
FIG. 3 shows the ultriviolet absorption spectrum of ML-236B exhibiting maxima at 229, 236 and 245 m$\mu$, respectively.
Figure 4:
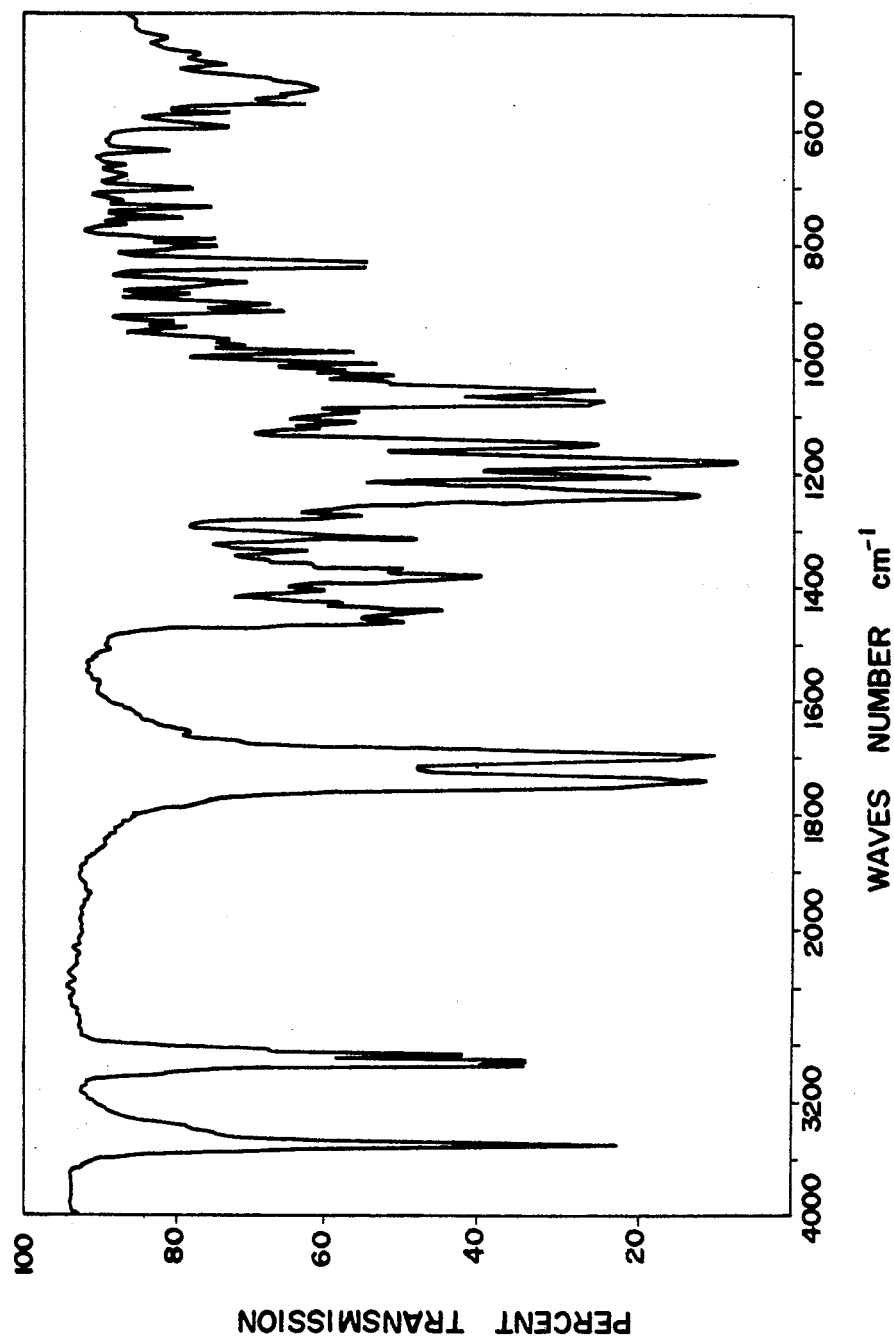
FIG. 4 shows the infrared absorption spectrum of ML-236B showing absorption bands at 3500, 1740 and 1695 cm$^{-1}$, respectively.
Figure 5:
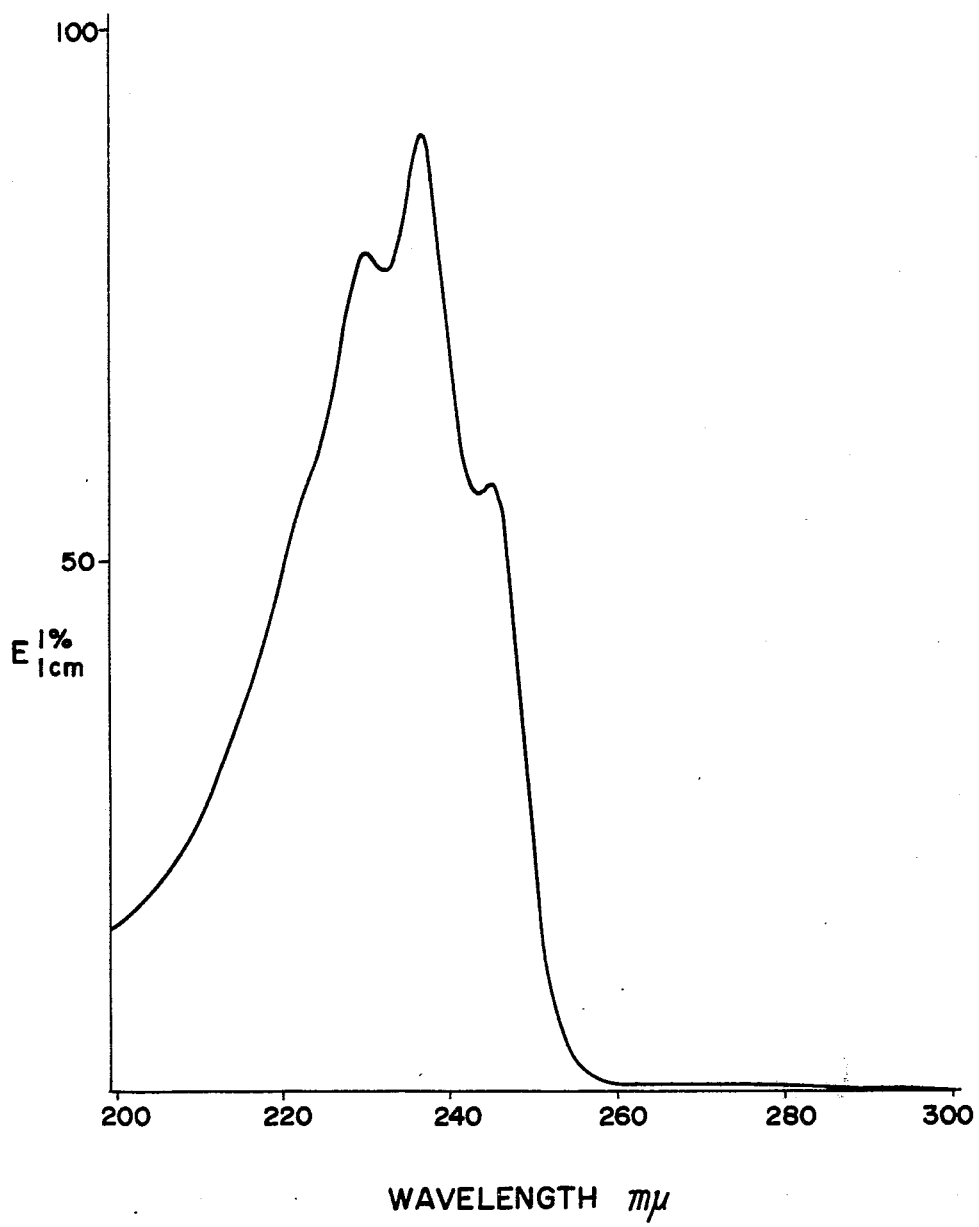
FIG. 5 shows the ultraviolet absorption spectrum of ML-236C exhibiting maxima at 229, 236 and 245 m$\mu$, respectively.

The substances ML-236 of this invention, when applied to patients suffering from such diseases as atheroscrelosis, hyperlipemia and so on, may be administered orally or parenterally in the form of a capsule, a tablet, an injectable preparation and the like and it is usually desirable to administer the substance via oral route. Doses may be varied depending upon the age, severity, body weight and other conditions of patients, but usual daily dosage for adult is within a range from about 200 mg. to 2000 mg. given in 3 or 4 divided doses. However, higher doses may be favourably applied, as required.

As fully disclosed hereinabove, the substances ML-236 of this invention have potent activities for the inhibition of cholesterol biosynthesis in vitro and in vivo.

I. The activity in vitro on inhibition of cholesterol biosynthesis of the substances ML-236 may be assayed by the following method. Slice of rat liver and radioactive acetic acid are brought to interaction at 37° C. for 60 minutes, the radioactive cholesterol thus biosynthesized is saponified and separated as precipitates with digitonin and then its radioactivity is measured to determine the produced cholesterol amount. Separately, the same procedures as above are employed except that ML-236 is added at the beginning of the reaction, thereby the biosynthesized cholesterol amount being determined. Thus, an effect of ML-236 can be quantitively determined. (See Bricker et al.: The Journal of Biological chemistry, 247, 4914, 1972).

According to the assay method as set forth above, it has been shown that the substances ML-236A, ML-236B and ML-236C exhibit about 50% inhibition of cholesterol biosynthesis at the respective concentrations of 0.04 $\mu$g./ml., 0.01 $\mu$g./ml. and 0.08 $\mu$g./ml. Further, acute toxicity of each substance ML-236 was determined in mice via intraperitoneal administrations to be 400 mg./kg. or more, which clearly shows a lower toxicity of the substance ML-236.

II. Effectiveness of ML-236 has been confirmed by examining its effect on lowering the lipid content in blood and liver of animals with various test methods, representatives of which will be more fully illustrated below.

1. One of two groups of rats having an average weight of about 200 g., each group consisting of 5 animals, was individually given by intraveneous injection with 200 mg./kg. of Triton WR 1339 (trade name; available from Ruger Chemical Co., Ltd., U.S.A.; having an activity of increasing cholesterol level in blood) simultaneously with intraperitoneal administration of 20 mg./kg. of ML-236B. After 24 hours from administration, rats were sacrificed by bleeding, blood and liver were collected and their cholesterol and neutral lipid levels were determined by a conventional method. As a result, it has been clear that cholesterol levels in blood are lowered by 14.2% and those in liver by 10.1%, as compared with those in the case of another group given with intravenous injection of Triton WR 1339 alone.

2. Two of four groups of rats, each group consisting of 5 animals, were orally given one dose of 5 mg./kg. of ML-236A suspended in gum arabic. After 3 hours and 18 hours from administration, animals were sacrificed by bleeding and blood was collected. Cholesterol and neutral lipid levels in blood serum were determined by a conventional method. It has been clear that the cholesterol and neutral lipid levels after 3 hours are lowered by 13.5% and 49.5%, respectively, and also that the cholesterol level after 18 hours is lowered by 13.5%, while lowering of neutral lipid level is not observed, as compared with those in the case of two other groups administered with gum arabic alone.

Moreover, one of two other groups of rats, each group consisting of 5 animals, were orally given 80 mg./kg. of powdery ML-236B in the form of a physiological saline solution. After 3 hours from administration, cholesterol and neutral lipid levels in blood serum were determined in the same manner as above. It has been clear that the cholesterol and neutral lipid levels are lowered by 20.0% and 44.2%, respectively, as compared with those in the case of another group administered with a physiological saline solution contacting no ML-236B.

It will be apparent from the above results that the substances ML-236 of this invention exhibit a prominent effect in the inhibition of cholesterol biosynthesis in a living body and thus they are utilized as a medicament against, for example, atherosclerosis, hyperlipemia and so on.

In another aspect of this invention, there is provided a process for producing physiologically active substances ML-237A, ML-236B and ML-236C which comprises cultivating an Ml-236-producing microorganism belonging to the genus *Penicillium* and then recovering said substances from a cultured broth.

The microorganisms which may be employed in this invention are the ML-236-producing ones belonging to the genus *Penicillium* and, as the strain proved to be particularly effective for this invention, there is, for instance, mentioned *Penicillium citrinum* SANK 18767 which has been deposited under an accession No. 2609 with Technical Research Institute of Microbial Industry, Agency of Industrial Science & Technology, Ministry of International Trade and Industry, Japan, and also as NRRL-8082 in the Northern Regional Research Laboratory, Northern Central Region, Agricultural Research Service, United States Department of Agriculture, at Peoria, Illinois, U.S.A.

Although this invention will be explained hereinbelow principally with respect of the strain SANK 18767, it is well-known in the art that various properties of all microorganisms belonging to the genus *Penicillium* are not definite, but the microorganisms of the genus *Penicillium* may be easily varied naturally and artificially. It is, accordingly, to be noted that all strains which are of the genus *Penicillium* and capable of producing ML-236, including varieties and mutants, are contemplated and usable in this invention.

The above strain SANK 18767, as mentioned above, is a Penicillium citrinum and the morphological properties of Penicillium citrinums are reported in the following literature: K. B. Raper and C. Thom; A Manual of the Penicillia, the Williams and Wilkins Company, 1949.

In carrying out the process of this invention, cultivation may be satisfactorily conducted under aerobic condition in the same manner as commonly employed in the art for cultivation of a strain of the genus Penicillium. For instance, the ML-236-producing microorganism may be grown in a culture medium, e.g., that containing malt extract 2%, glucose 2%, peptone 1%, agar 2% and then the culture so obtained may be inoculated and cultivated in a culture medium. Alternatively, the microorganism grown in a culture medium may be cultivated in another fresh culture medium to produce ML-236.

As medium components may be employed any of the well-known nutrient materials for Penicillium. For instance, as an assimilable carbon source, glucose, glycerol, maltose, dextrin, starch, lactose, sucrose, molasses, soybean oil, cotton seed oil, etc., preferably glucose and maltose may be employed and, as an assimilable nitrogen source, soybean meal, peanut meal, cotton seed meal, fish meal, corn steep liquor, peptone, rice bran, meat extract, yeast, yeast extract, sodium nitrate, ammonium nitrate, ammonium sulfate, etc. may be used. And, such inorganic salts as sodium chloride, phosphates, calcium carbonate, etc. may be added to a culture medium. A minor amount of a metal salt may also be added, if necessary. Further, a minor amount of a heavy metal may be added, if necessary.

Particularly, in cultivating the ML-236-producing microoranisms under aerobic condition, ordinary aerobic cultivation methods such as, for example, solid culture, culture under aeration and agitation, shaken culture etc. may be favourably utilized.

In carrying out cultivation with aeration and agitation, an anti-foaming agent, e.g., silicon oil, vegetable oils, surfactants, etc. may be suitably employed.

The pH of the medium may be usually within a pH range of 3-9 and preferably within or around neutral range and cultivation temperatures may be usually of 20°-30° C., in particular about 28° C. being preferred.

Cultivation may be continued until ML-236 will be substantially accumulated in a culture medium, usually for 20 hours to 240 hours, preferably for 48 hours to 168 hours and, after cultivation, each ML-236 substance may be isolated and recovered from a cultured broth by a suitable combination of various methods related to the properties thereof which has been elucidated by us, as illustrated in the examples given below. For example, there may be mentioned extraction with an organic solvent, e.g., ether, ethyl acetate or chloroform; dissolution into a more polar solvent, e.g., acetone or alcohol; removal of impurities with a less polar solvent, e.g., petroleum ether or hexane; adsorptive chromatography with active carbon or silica gel; gel filtration through a column of "Sephadex" (trade name; available from Pharmacia Co., Ltd., U.S.A.); and so on. By the use of a suitable combination of these measures can be isolated from a cultured broth.

The present invention will be more fully illustrated by way of the following examples, but they are not intended to limit the scope of this invention. Various modifications of the present process may be made by those skilled in the art, in particular, for the recovery of ML-236A, ML-236B and ML-236C from a cultured broth, in view of the above-described properties.

EXAMPLE 1

Into a 600 l.-volume fermenter was charged 300 . of a culture medium containing glucose 2%, peptone ("Kyokuto," trade name; available from Kyokuto Seiyaku K.K., Japan) 0.1% and malt extract 3% and Penicillium citrinum SANK 18767 was inoculated thereon. Cultivation was conducted at a temperature of 28° C., an aeration of 300 l./min. and an agitation of 190 r.p.m. for 91 hours.

The cultured broth was filtered by a filter press to give 280 l. of the filtrate. The filtrate so obtained was adjusted to pH 4.0 with 6N hydrochloric acid and extracted twice with 250 l. of ethyl acetate.

The extract was concentrated to dryness under reduced pressure to give 150 g. of the dried product. 120 g. of the product was adsorbed on a column of 1040 g. of silica gel ("Wakogel C-200"; trade name; Wako Junyaku K.K., Japan), which was developed in turn with 5 l. of benzene, 7.5 l. of benzene - ethyl acetate (95:5) and then 28 l. of benzene - ethyl acetate (80:20). Active eluates are of two fractions, namely the first eluted fraction named C (containing ML-236C) an the second eluted fraction named B (containing ML-236B). Further, the column was developed with 2 l. of acetone to give the third fraction named A (containing ML-236A). The former two fractions were concentrated to dryness so that 2.42 g. and 2.61 g. of the dried products were obtained from the fractions C and B, respectively.

The fraction B (2.61 g.) was dissolved in 100 ml. of benzene, the resulting solution was washed with 100 ml. of water and the washings were discarded. The benzene layer was dried over sodium sulfate an concentrated and the residue was allowed to stand overnight, whereupon the so separated crystalline substance was recovered. The substance was then recrystallized once from benzene and subsequently once from ethanol to give 232 mg. of ML-236B in a pure state as white crystals. This substance was confirmed as pure by a thin-layer chromatography and shows an inhibitory activity of about 50% on biosynthesis of cholesterol in a concentration of 0.01 μg./ml.

EXAMPLE 2

Into a 6 ton-volume fermenter was charged 3000 l. of the same culture medium is in Example 1 and Penicillium citrinum SANK 18767 was inoculated thereon. Cultivation was conducted for 90 hours in the same manner as in Example 1. The cultured broth was filtered by a filter press to give 2590 l. of the filtrate. The filtrate was concentrated under reduced pressure to 450 l. and the concentrate was adjusted to pH 4.0 with 6N hydrochloric acid and then extracted with 450 l. of ethyl acetate. 390 l. of the extract was concentrated to dryness to yield 346 g. of an oily substance. The substance was adsorbed on a column of 5.18 kg. of silica gel ("Wakogel C-200"), which was then developed in turn with 98 l. of n-hexane, 60 l. of n-hexane - acetone (95:5) and then 150 l. of n-hexane - acetone (85:15). The resulting active fraction (42 l.; containing ML-236B and other active substances) was concentrated to dryness to leave 40 g. of the dried product. This product was dissolved in a suitable amount of benzene and insolubles were filtered off. The filtrate was left overnight, whereupon ML-236B was separated out as crystals and other active substances were retained in a waste solution. The crystals were collected by filtration and then recrystallized once from benzene and subsequently once from ethanol to obtain 12.8 g. of the pure ML-236B.

EXAMPLE 3

Into a 6 ton-volume fermenter was charged 3000 l. of a culture medium containing glucose 2%, peptone ("Kyokuto") 0.1% and malt extract 3% and Penicillium citrinum SANK 18767 was inoculated thereon. Cultivation was conducted at a temperature of 28° C., an aeration of 3000 l./min. and an agitation of 145 r.p.m. for 96 hours.

The cultural broth was filtered by a filter press to give 2900 l. of the filtrate. The filtrate so obtained was concentrated under reduced pressure to 450 l. and the concentrate was then adjusted to pH 4.0 with 6N hydrochloric acid followed by extraction with 500 l. of ethyl acetate. 500 l. of the extract was concentrated to dryness to leave 327 g. of an oily substance. The substance was adsorbed on a column of 5.5 kg. of silica gel ("Wakogel C-200"), which was then developed in turn with 10 l. of n-hexane, 60 l. of n-hexane - acetone (95:5) and then 150 l. of n-hexane - acetone (85:15). Two active fractions were given, namely, the first eluted fraction containing ML-236C and the second eluted fraction containing ML-236B.

Thereafter, the column was developed with 20 l. of acetone, thereby eluting the third active fraction containing ML-236A.

Each respective fraction was individually concentrated to dryness.

The dried product (194 g.) from the ML-236A fraction was dissolved in 2 l. of ethyl acetate and the resulting solution was extracted three times with 500 ml. portion of a saturated aqueous solution of sodium carbonate. The ethyl acetate layer was separated, further washed with a saturated aqueous solution of sodium chloride, dried over anhydrous sodium sulfate and then concentrated to dryness to leave 70 g. of the dried product. The product was adsorbed on a column of 150 g. of silica gel ("Wakogel C-200"), which was then washed with 1 l. of benzene and 3 l. of benzene - ethyl acetate (8:2) and eluted with 5 l. of benzene - methanol (95:5). Main fractions were concentrated to dryness to give 9 g. of ML-236A as an oily substance.

The dried product (38 g.) from the ML-236B fraction was added to 500 ml. of benzene and insolubles were removed by filtration. The filtrate was concentrated and the concentrate was allowed to stand overnight, whereupon ML-236B was separated out as crystals. The so separated crystals were recovered by filtration and crystallized once from benzene and subsequently once from ethanol to give 10.5 g. of ML-236B in a pure state.

Finally, the dried product (3.2 g.) from the ML-236C fraction was dissolved in a small amount of dichloromethane and the resulting solution was adsorbed on a column of 50 g. of silica gel ("Wakogel C-200"), which was then developed in turn with 500 ml. of dichloromethane and then dichloromethane - ethyl acetate (95:5). Fractions containing ML-236C were collected and concentrated to dryness to give 2.1 g. of ML-236C as an oily substance.

What is claimed is:

1. A process for the production of substances, ML-236A, ML-236B and ML-236C having the formulae, respectively,

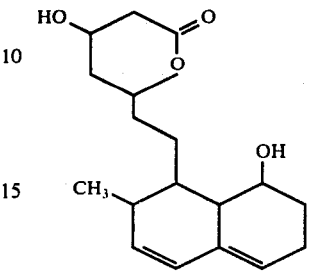

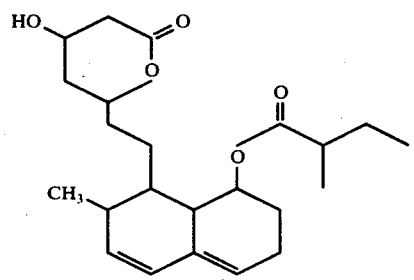

and

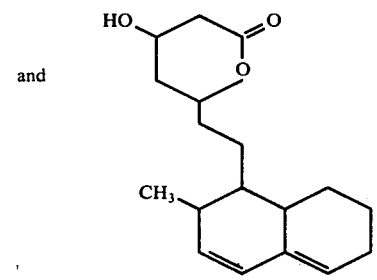

which comprises cultivating an ML-236-producing microorganism belonging to the genus *Penicillium* in a culture medium under aerobic condition and recovering said ML-236 substances from the cultured broth.

2. A process according to claim 1 wherein said microorganism is *Penicillium citrinum* SANK 18767.

3. A process according to claim 1 wherein said cultivation is effected at a temperature ranging from 20° C. to 30° C.

4. A process according to claim 1 wherein the pH of said culture medium is within a range of 3 to 9.

5. A process according to claim 1 wherein cultivation period is within a range of 20 hours to 240 hours.

* * * * *

PAGE ONE OF TWO PAGES

UNITED STATES PATENT AND TRADEMARK OFFICE
CERTIFICATE OF CORRECTION

PATENT NO. : 4,049,495
DATED : September 20, 1977
INVENTOR(S) : AKIRA ENDO et al It is certified that error appears in the above-identified patent and that said Letters Patent are hereby corrected as shown below:

In the title: delete and replace with --- Fermentative Process for Producing Physiologically Active Substances ---.

Column 1, line 5: delete "(X)".

Column 1, lines 53-54: replace "hypochloesteremic" with --- hypocholesteremic ---.

Column 3, line 3: replace "ultriviolet" with --- ultraviolet ---.

Column 3, line 40: replace "chemistry" with --- Chemistry ---.

Column 4, line 53: after "respect", replace "of" with --- to ---.

Column 5, line 54: after "measures", insert --- the crystalline or oily form of the present substance ---.

Column 5, line 65: after "300", delete the period and replace with --- 1. ---.

UNITED STATES PATENT AND TRADEMARK OFFICE
CERTIFICATE OF CORRECTION

PATENT NO. : 4,049,495
DATED : September 20, 1977
INVENTOR(S) : AKIRA ENDO et al It is certified that error appears in the above—identified patent and that said Letters Patent are hereby corrected as shown below:

Column 6, lines 16 and 26: replace "an" with --- and ---.

Column 6, line 39: after "medium", replace "is" with --- as ---.

*Signed and Sealed this*

*Twenty-first* Day of *March 1978*

[SEAL]

Attest:

RUTH C. MASON
*Attesting Officer*

LUTRELLE F. PARKER
*Acting Commissioner of Patents and Trademarks*